United States Patent

Jäger et al.

[11] Patent Number: 5,502,173
[45] Date of Patent: Mar. 26, 1996

[54] PROCESS FOR THE PREPARATION OF A SUBSTITUTED 2-AMINO-1-SULPHONAPHTHALENE

[75] Inventors: Horst Jäger, Leverkusen; Siegbert Arnold, Bonn; Richard Sommer, Odenthal-Gloebusch, all of Germany

[73] Assignee: Bayer Aktiengesellschaft, Leverkusen, Germany

[21] Appl. No.: 312,578

[22] Filed: Sep. 27, 1994

Related U.S. Application Data

[63] Continuation of Ser. No. 32,880, Mar. 18, 1993, abandoned, which is a continuation of Ser. No. 815,110, Dec. 30, 1991, abandoned.

[30] Foreign Application Priority Data

Jan. 10, 1991 [DE] Germany .................. 41 00 513.9

[51] Int. Cl.⁶ .................. C09B 62/085; C09B 62/09; C09B 19/00; C07D 251/50
[52] U.S. Cl. .................. 534/598; 534/632; 534/887; 534/581; 544/76; 544/208
[58] Field of Search .................. 534/598, 632; 544/76, 208

[56] References Cited

U.S. PATENT DOCUMENTS

| 4,126,609 | 11/1978 | Jager | 534/632 X |
|---|---|---|---|
| 4,189,576 | 2/1980 | Altorfer et al. | 534/632 X |
| 4,740,597 | 4/1988 | Franke et al. | 534/632 X |
| 5,091,515 | 2/1992 | Herd et al. | 534/598 |

FOREIGN PATENT DOCUMENTS 0111358  11/1980  Japan .................. 544/211

*Primary Examiner*—Floyd D. Higel
*Attorney, Agent, or Firm*—William C. Gerstenzang; Sprung Horn Kramer & Woods

[57] ABSTRACT

2,4,6-trifluoro-5-chloro-pyrimidine and the aqueous solution of a salt of 2-amino-5-aminomethyl-naphthalene-1-sulphonic acid are simultaneously metered into a reactor in approximately equimolar amounts and afford a valuable intermediate for the preparation of high-purity dyes.

11 Claims, No Drawings

PROCESS FOR THE PREPARATION OF A SUBSTITUTED 2-AMINO-1-SULPHONAPHTHALENE

This application is a continuation of application Ser. No. 08/032,880, filed on Mar. 18, 1993, now abandoned, which is a continuation of application Ser. No. 07/815,110, filed Dec. 30, 1991, now abandoned.

The invention relates to a process for the preparation of a 2-amino-1-sulphonaphthalene which is substituted by a reactive group, and to the use of the substances thus obtained for the preparation of a reactive dye.

Dyes based on 1-sulpho-2-amino-naphthalene into which reactive groups are introduced after the diazotisation and coupling have already been disclosed in DE-A 2 264 698. This preparation is in need of improvement especially in respect of the purity of the corresponding end products. 2-Amino-5-(2',4'-difluoro-5'-chloro-pyrimidin-6'-yl)-amino-methyl- naphthalene-1-sulphonic acid has already been disclosed as diazo component in DE-A 3 223 257 and DE-A 2 831 912.

The invention relates to an improved process for the preparation of compounds of the formula

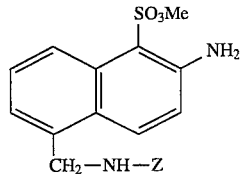

(1)

in which
Z=a fibre-reactive radical of a reactive component which contains at least one reactive fluorine atom, especially a radical of the pyrimidine or amino-triazine series and
Me=a cation, especially Li, Na, K or H characterised in that a fluorine-containing reactive component of the formula Z–F (2) (F=fluorine)

and an aqueous solution of a salt, especially of an alkali metal salt, of 2-amino-5-amino-methyl-naphthalene-1-sulphonic acid (3) is metered into a reactor, the reactive component (2) and the sulphonic acid (3) being metered simultaneously into the reactor with reaction.

The reactants are preferably metered in together simultaneously in a molar ratio of approximately 1:1 at temperatures from −5° C. to 50° C., the temperature depending on the reactivity of the reactive components (2), and in a pH range of 8–11, preferably 9–10, especially 9.3–9.7.

This can be carried out without first introducing any of reactants (2) and (3). It is, however, advantageous to initially introduce 1–20%, especially 5–15% of (2), based on the total amount of (2), and to meter in the remainder at the same rate as the solution of (3).

The process can be carried out continuously or batchwise. The batchwise procedure is carried out in a manner such that an aqueous solution of an alkali metal salt (3), a reactive component (2) and, where appropriate, alkali which serves to maintain the stated pH range, are metered into the aqueous contents of the reactor. The molar ratio of (2) to (3) is generally 1.2-1.0:1.0, especially 1.1-1.0:1.

The reaction is preferably carried out such that the initial aqueous contents of the reactor include a buffer which is suitable for the pH range of 8–11. The amount of buffer should be such that adequate buffering is guaranteed. 0.1–2.0 moles of buffer are used per mole of alkali metal salt (3). Suitable buffer systems are phosphates, carbonates and borates. It is preferable to use alkali metal borates.

Suitable alkalis which can be used for maintaining the pH range are aqueous solutions of the alkali metal hydroxides, such as lithium hydroxide, sodium hydroxide or potassium hydroxide. It is also possible to initially introduce an amount of buffer substance such that a correction of the stated pH range using alkali is not necessary during the acylation.

Examples of reactive components (2) are:
Aminotriazine series:
2,4-difluoro-6-(o-, m-, p-sulphophenyl)-amino-triazine, 2,4-difluoro-6-methoxytriazine, 2,4-difluoro-6-(2',5'-di-sulphophenyl)-amino-triazine, 2,4-difluoro-6-(6'-sulphonaphth-2'-yl)-amino-triazine, 2,4-difluoro-6-(2'-methyl-5'-sulphophenyl)-amino-triazine, 2,4-difluoro-6-(2'-meth-yl-4'-sulphophenyl)-amino-triazine, 2,4-difluoro-6-(2'-chloro-4'-sulphophenyl)-amino-triazine, 2,4-difluoro-6-(2'-methoxy-4'-sulphophenyl)-amino-triazine, 2,4-di-fluoro-6-(o-, m-, p-carboxyphenyl)-amino-triazine, 2,4-difluoro-6-(1'-sulphonaphth-2'-yl)-amino-triazine, 2,4-difluro-6-aminotriazine, 2,4-difluoro-6-methylamino-triazine, 2,4-difluoro-6-ethylaminotriazine, 2,4-di-fluoro-6-methoxyethoxytriazine, 2,4-difluoro-6-β-methoxyethylaminotriazine.

Pyrimidine series:
2,4-difluoro-6-methylpyrimidine, 2,6-difluoro-4-methyl-5-chloro-pyrimidine, 2,4-difluoro-5-ethylsulphonyl-pyrimidine, 2,6-difluoro-4-chloro-pyrimidine, 2,4,6-tri-fluoro-5-chloro-pyrimidine, 2,6-difluoro-4-methyl-5-bromopyrimidine, 2,6-difluoro-5,6-dichloro- or -dibromopyrimidine, 4,6-difluoro-2,5-dichloro- or -dibromopyrimidine, 2,6-difluoropyrimidine, 2,4,6-trifluoro-5-chloro-methylpyrimidine, 2,6-difluoro-5-methyl-4-chloropyrimidine, 2,6-difluoro-5-chloropyrimidine, 2,4,6-trifluoro-5-methylpyrimidine, 2,4-difluoro-5-cyano-pyrimidine, 2,4-difluoro-5-methyl-pyrimidine, 2,4-difluoro-5-trifluoromethylpyrimidine, 2,4-difluoro-5-methylsulphonylpyrimidine, 2,4-difluoro-5-phenyl-pyrimidine, 4,6-difluoro-2-methyl-pyrimidine, 4,6-di-fluoro-6-chloro-2-methylpyrimidine, 4,5,6-trifluoro-pyrimidine, 4,6-difluoro-6-chloro-2-trifluoromethyl-pyrimidine, 4,6-difluoro-2-phenylpyrimidine, 4,6-di-fluro-5-cyano-pyrimidine, 4,6-difluoro-5-nitro-pyrimidine, 4,6-difluoro-5-methylsulphonylpyrimidine, 4,6-difluoro-5-phenylsulphonylpyrimidine, 4,6-difluoro-5-phenylsulphonylpyrimidine, 4,6-difluoro-5-chloropyrimidine.

Most particularly preferred is an improved process for the preparation of a compound of the formula

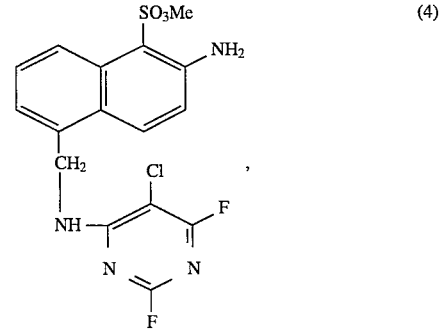

(4)

in which
Me=a cation, especially Li, Na, K or H, characterised in that 2,4,6-trifluoro-5-chloropyrimidine and an aqueous solution of a salt, especially an alkali metal salt, of 2-amino-5-amino-methyl-naphthalene-1-sulphonic acid (3) are metered into a reactor, the pyrimidine and the sulphonic acid (3)

being metered simultaneously into the reactor with reaction. The reactants are preferably metered in together simultaneously in a molar ratio of approximately 1:1 at temperatures from −5° C. to 20° C., preferably at −2° C. to 5° C. and in a pH range of 8–11, preferably 9–10, especially 9.3–9.7.

The invention further relates to a process for the preparation of the dyes of the formula

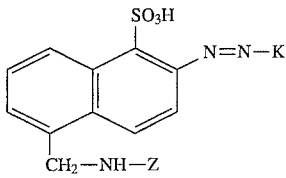

(5)

in which

K is the radical of a coupling component HK (6), characterised in that the amines (1) prepared according to the invention, which are preferably present in the form of an aqueous slurry, are diazotised and coupled onto coupling component (6).

Most particularly preferred is a process for the preparation of dyes of the formula

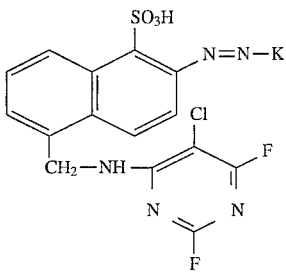

(7)

in which

K is the radical of a coupling component HK (6), characterised in that the amine (4) prepared in accordance with the invention, which is preferably present in the form of an aqueous slurry, is diazotised and coupled onto coupling component (6).

This process is preferably carried out such that the diazotisation takes place in the presence of an anionic dispersant. This is generally employed in amounts of from 20 to 200 g, especially from 70 to 150 g, per mole of the amine (1) to be diazotised. Anionic dispersants are ligninsulphonates and condensation products of aromatic sulphonic acids with formaldehyde. Particularly suitable are the sodium salts of the condensation products of naphthalenesulphonic acid with formaldehyde.

The diazotisation is carried out in water by the direct or indirect method (see Houben-Weyl volume 10, part 3, pp. 16–24; 4th edition).

The nitrite can be added in the form of an aqueous sodium or lithium nitrite solution.

In the indirect method the amine (1) is dissolved in water under neutral conditions, the stoichiometric amount of a nitrite is added and this mixture is then added to an initial mixture of water and acid.

In the direct diazotisation, the calculated amount of a nitrite is gradually added to the suspension of the amine (1) in water, after the addition of an acid, until the end point of the reaction is reached.

The dyes can be isolated by the addition of a salt and can be dried. It is equally possible to prepare concentrated aqueous solutions from the preparation solutions or suspensions by subjecting these solutions or suspensions in water to a demineralisation, for example by pressure permeation. The preparation solutions or suspensions are preferably brought directly to dryness, if appropriate after a pressure permeation.

The invention thus further relates to bringing the aqueous solutions or suspensions of the dyes (5) formed after the coupling directly to dryness without intermediate isolation, if appropriate after the addition of conventional standardising agents for reactive dyes. This can be carried out by evaporation. The preparation mixtures may also be passed through a drum dryer. The dye is preferably isolated by spray drying.

Coupling components HK (6) are, in particular, suitable compounds from the aminobenzene and naphthalene series, for example anilines, N-mono-substituted anilines, m-phenylenediamine derivatives, aminonaphthalenes, aminonaphthalenesulphonic acids, naphtholsulphonic acids or aminonaphtholsulphonic acids, furthermore pyrazolones, aminopyrazoles, aminopyridines, hydroxypyridines/pyridones, hydroxypyrimidines, indoles, barbituric acid derivatives or acetoacetarylides.

Preferred coupling components HK are compounds of the formula

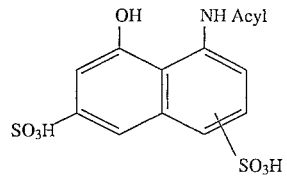

(7)

in which

Acyl=an acyl group, such as alkylcarbonyl, alkylsulphonyl, arylcarbonyl or arylsulphonyl, alkyl preferably representing $C_1$-$C_4$-alky optionally substituted by $C_1$-$C_4$-alkoxy, Cl, COOH or or $SO_3H$, and aryl preferably representing phenyl optionally substituted by $C_1$-$C_4$-alkyl, $C_1$-$C_4$-alkoxy or Cl.

Acyl is in particular benzoyl.

The formulae of the water soluble compounds in the description and in the examples are those of the free acids. The substances are generally isolated and used in the form of their alkali metal salts, especially in the form of the lithium, sodium or potassium salts.

Example 1

Acylation 252 g of 2-amino-5-aminomethyl-naphthalene-1-sulphonic acid (1.0 mol; in the form of betaine) are dissolved in 1,800 ml of water by adding 1 mol of sodium hydroxide solution. 38 g of boric acid (0.61 mol) are dissolved in 400 ml of water with 0.38 mol of sodium hydroxide solution at pH 9.5 to form the initial reactor contents. 1 kg of ice is subsequently added. 177 g of 2,4,6-trifluro-5-chloro-pyrimidine and the alkaline solution of the 2-amino-5-aminomethyl-naphthalene-1-sulphonic acid are simultaneously metered into the initial contents of the reactor with good stirring in the course of 20 minutes. The temperature is maintained at 0° C. by adding ice. In order to maintain the pH range of 9.5 (9.3 to 9.7), approximately 0.9 mol of sodium hydroxide solution must be added during the acylation. Stirring is continued for approximately 1 hour, the pH still having to be adjusted slightly. The condensation product is partially precipitated. Volume 6 l.

Diazotisation, Coupling, Isolation

To this suspension are added 120 g of an anionic dispersant (sodium salt of the condensation product of naphthalenesulphonic acid and formaldehyde) and diazotisation is then carried out directly in a known manner. The amount of coupling component is dependent on the nitrite consumption in the case of the direct diazotisation. This amount of 1-hydroxy-8-benzoylamino-naphthalene-3,5-disulphonic acid is initially introduced into approximately 1500 ml of water and the diazotisation is added, a neutral pH range being maintained by the addition of sodium bicarbonate or sodium carbonate. After coupling is complete, conventional standardising agents for reactive dyes (anionic dispersants, monosodium/disodium phosphate buffers, dedusting agents) may be added to the aqueous coupling mixture, and the mixture is spray dried directly.

The dye corresponds to the formula

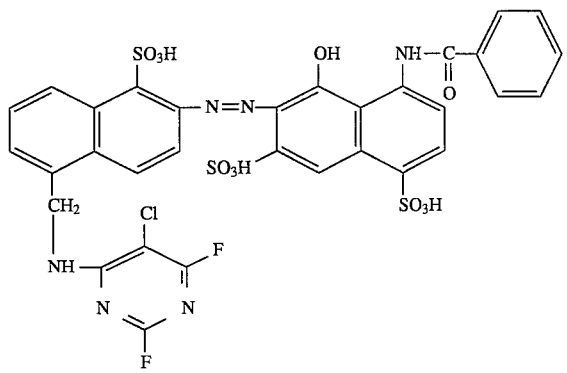

The dye is disclosed in DE-A 2 232 541 (Example 3).

When 1-hydroxy-8-benzoylamino-naphthalene-3,6-disulphonic acid is used in place of 1-hydroxy-8-benzoylamino-naphth-alene-3,5-disulphonic acid the corresponding dye is likewise obtained in high yield.

Example 2

The acylation mixture obtained according to Example 1, paragraph 1 is adjusted to pH 7.5 and heated to approximately 55°–60° C., the acylation product going into solution. 1.0 mol of sodium nitrite is then added in the form of a 30% strength aqueous solution and the mixture is allowed to run into an initial mixture comprising water, 120 g of the anionic dispersant used in Example 1 and hydrochloric acid, the temperature being maintained between 10° and 20° C. by means of ice. The coupling onto 1-hydroxy-8-benzoyl-amino-naphthalene-3,5-disulphonic acid takes place in the manner described in Example 1. After coupling is complete, the coupling mixture is spray dried directly, if desired after concentration by pressure permeation.

Example 3

252 g of 2-amino-5-aminomethyl-naphthalene-1-sulphonic acid (1.0 mol; in the form of betaine) are dissolved in 1,800 ml of water by adding 1 mol of sodium hydroxide solution. 38 g of boric acid (0.61 mol) are dissolved in 400 ml of water with 0.38 mol of sodium hydroxide solution at pH 9.5 to form the initial reactor contents. 1 kg of ice is subsequently added. 10 g of 2,4,6-tri-fluoro-5-chloro-pyrimidine followed by 170 g of 2,4,6-trifluoro-5-chloro-pyrimidine and the alkaline solution of the 2-amino-5-aminomethyl-naphthalene-1-sulphonic acid are simultaneously metered into the initial contents of the reactor with good stirring in the course of 20 minutes. The temperature is maintained at 0° C. by adding ice. In order to maintain the pH range of 9.5 (9.3 to 9.7), approximately 0.9 mol of sodium hydroxide solution must be added during the acylation. Stirring is continued for approximately 1 hour, the pH still having to be adjusted slightly. The condensation product is partially precipitated. Volume 6 l.

Example 4

252 g of 2-amino-5-aminomethyl-naphthalene-1-sulphonic acid (1.0 mol; in the form of betaine) are dissolved in 1,800 ml of water by adding 1 mol of sodium hydroxide solution. 38 g of boric acid (0.61 mol) are dissolved in 400 ml of water with 0.38 mol of sodium hydroxide solution at pH 9.5 to form the initial reactor contents. Approximately 200 g of ice are then added in order to bring the temperature to 15° C.

151 g of 4,6-difluoro-5-chloro-pyrimidine and the alkaline solution of the 2-amino-5-aminomethyl-naphthalene-1-sulphonic acid are simultaneously metered into the initial contents of the reactor with good stirring in the course of 20 minutes. The temperature is maintained at 15° C. by adding ice. In order to maintain the pH range of 9.5 (9.3 to 9.7), approximately 0.9 mol of sodium hydroxide solution must be added during the acylation. Stirring is continued for approximately 1 hour, the pH still having to be adjusted slightly. The condensation product is partially precipitated. Volume 5 l.

Diazotisation, coupling and isolation are carried out as stated in Example 1. The resulting dye corresponds to the formula

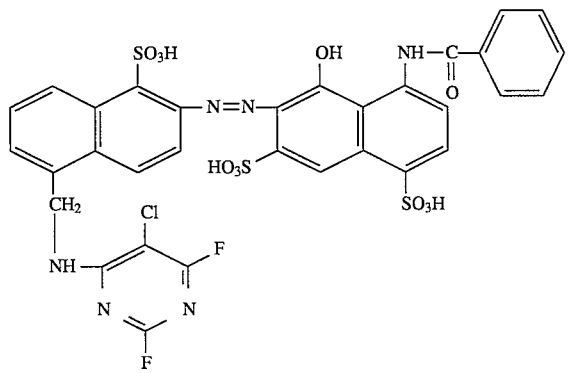

Example 5

Acylation 252 g of 2-amino-5-aminomethyl-naphthalene-1-sulphonic acid (1.0 mol; in the form of betaine) are dissolved in 1,800 ml of water by adding 1 mol of sodium hydroxide solution. 38 g of boric acid (0.61 mol) are dissolved in 400 ml of water with 0.38 mol of sodium hydroxide solution at pH 9.5 to form the initial reactor contents. 1 kg of ice is subsequently added. The ice-cold solution of the monocondensation product prepared from 1.05 mol of o-sulphanilic acid and 1.1 mol of 2,4,6-trifluorotriazine according to the details of Example 2 of German Offenlegungsschrift 2 556 640 and the alkaline solution of the 2-amino-5-aminomethyl-naphthalene-1-sulphonic acid are simultaneously metered into the initial contents of the reactor with good stirring in the course of 20 minutes. The temperature is maintained at 0° C. by adding ice. In order to maintain the pH range of 9.5 (9.3 to 9.7), approximately 0.9 mol of sodium hydroxide solution must be added during the acylation. Stirring is continued for approximately 1 hour, the pH still having to be adjusted slightly. The condensation product is dissolved.

Diazotisation, Coupling, Isolation

To this solution are added 100 g of an anionic dispersant (sodium salt of the condensation product of naphthalene-sulphonic acid and formaldehyde) and diazotisation is then carried out directly at 0°–5° C. in a known manner. The amount of coupling component is dependent on the nitrite consumption in the case of the direct diazotisation. This amount of 1-hydroxy-8-benzoylamino-naphthalene-3,5-disulphonic acid is initially introduced into approximately 1500 ml of water and the diazotisation is added, a neutral pH range being maintained by the addition of sodium bicarbonate or sodium carbonate. After coupling is complete, conventional standardising agents for reactive dyes (anionic dispersants, monosodium/disodium phosphate buffers, dedusting agents) may be added to the aqueous coupling mixture, and the mixture is spray dried directly.

The dye corresponds to the formula

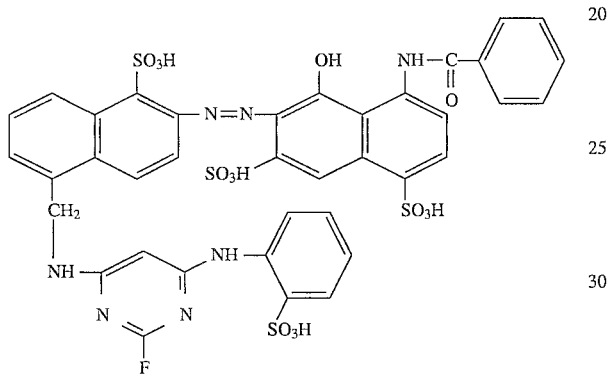

The dye is disclosed in DE-A 2 847 173 (Example 1).

When 1-hydroxy-8-benzoylamino-naphthalene-3,6-disulphonic acid is used in place of 1-hydroxy-8-benzoylamino-naph-thalene-3,5-disulphonic acid the corresponding dye is likewise obtained in high yield.

We claim:

1. Process for the preparation of a compound of the formula

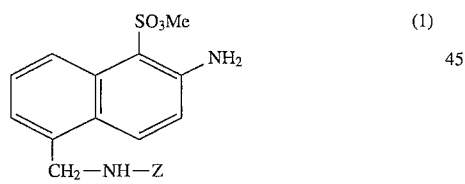

in which

Z=a radical of a fiber-reactive pyrimidine or aminotriazine radical component which contains at least one reactive fluorine atom, and Me=Li, Na, K or H characterised in that a fluorine-containing reactive component of the formula Z—F (2) (F=fluorine)

and an aqueous solution of an alkali metal salt, of 2-amino-5-amino-methyl-naphthalene-1-sulphonic acid (3) is metered into a reactor, the reactive component (2) and the sulphonic acid (3) being metered simultaneously into the reactor with reaction wherein the pH is 8 to 11 at the beginning and during the reaction.

2. Process according to claim 1
characterised in that the reactants are metered together simultaneously in a molar ratio of approximately 1:1 at temperatures from –5° C. to 50° C. and in a pH range of 8 to 11.

3. Process according to claim 1
characterised in that 1 to 20% of reactive component (2), based on the total amount of (2), is initially introduced, and the remainder of (2) is metered in simultaneously with the solution of (3).

4. Process according to claim 1
characterised in that the reaction solution contains an alkali metal borate as buffer.

5. Process according to claim 1
characterised in that compound (1) corresponds to the following formula

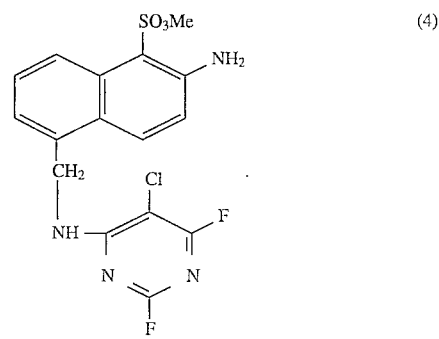

6. Process for the preparation of dye of the formula

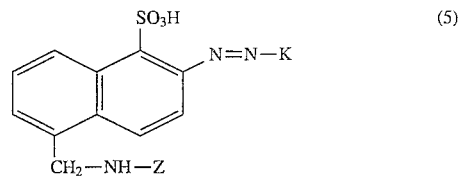

in which

Z has the meaning indicated in claim 1 and

K represents the radical of a coupling component HK characterised in that the compound of the formula (1) prepared according to at least one of the preceding claims is diazotised and subsequently coupled with the coupling component HK.

7. Process according to claim 6, characterised in that the diazotisation is carried out in the presence an anionic dispersant.

8. Process according to claim 6,
characterised in that the dye solution or suspension formed after the coupling is brought directly to dryness, after the addition of standardising agents for reactive dyes.

9. Process for the preparation of dyes according to claim 6, characterised in that K represents the radical

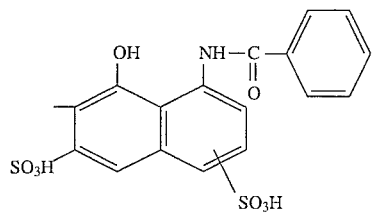

and Z represents

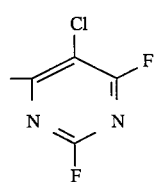
10. The process of claim 1, wherein the compound of formula (1) is
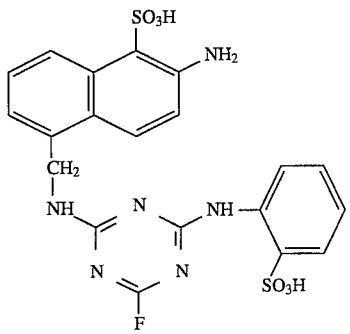
and Z-F represents the monocondensation product of 0-sulphanilic acid and 2,4,6-trifluorotriazine and said alkali metal salt is sodium salt.
11. The process of claim 1 wherein said compound of formula (1) is
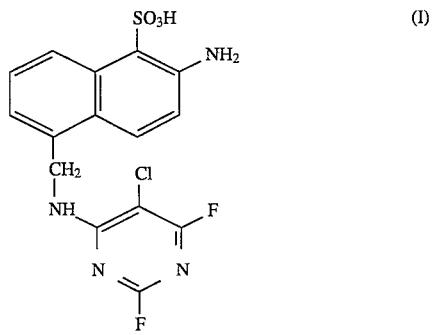
and Z-F represents 2,4,6-trifluoro-5-chloro-pyrimidine and said alkali metal salt is sodium salt.
* * * * *